United States Patent [19]

Velenyi et al.

[11] 4,380,672

[45] Apr. 19, 1983

[54] CONVERSION OF 2-PHENYL PROPANAL TO 2-INDANONE

[75] Inventors: Louis J. Velenyi, Lyndhurst; Andrew S. Krupa, Twinsburg, both of Ohio

[73] Assignee: The Standard Oil Company, Cleveland, Ohio

[21] Appl. No.: 345,264

[22] Filed: Feb. 2, 1982

Related U.S. Application Data

[63] Continuation-in-part of Ser. No. 182,282, Aug. 28, 1980, Pat. No. 4,329,506.

[51] Int. Cl.$^3$ .............................................. C07C 45/67
[52] U.S. Cl. .................................................... 568/310
[58] Field of Search ........................ 568/310, 312, 327

[56] References Cited

U.S. PATENT DOCUMENTS

| | | | |
|---|---|---|---|
| 3,384,668 | 5/1968 | Canter et al. | 568/388 |
| 3,453,331 | 7/1969 | Hargis et al. | 568/388 |
| 3,966,822 | 6/1976 | Fukui et al. | 568/388 |
| 4,200,589 | 4/1980 | Scharf | 568/389 |

*Primary Examiner*—James H. Reamer
*Attorney, Agent, or Firm*—Gary R. Plotecher; Herbert D. Knudsen; Larry W. Evans

[57] ABSTRACT

2-phenyl propanal is converted to 2-indanone by contact at conversion conditions, typically vapor-phase conditions, with a catalyst of the formula $Mo_{12} Cu_{0.1-10} V_{0.1-5} W_{0.1-3} M_{0-3} O_x$ where M is an optional promoter, such as Sn, Sb, Te or a Group VIII element.

5 Claims, No Drawings

CONVERSION OF 2-PHENYL PROPANAL TO 2-INDANONE

This application is a continuation-in-part of Ser. No. 182,282, filed 8-28-80, now U.S. Pat. No. 4,329,506.

BACKGROUND OF THE INVENTION

1. Field of the Invention

This invention relates to the conversion of an aldehyde to a cyclic ketone.

2. Description of the Prior Art

Canter, et al., U.S. Pat. No. 3,384,668, teach the isomerization of aliphatic aldehydes to ketones by contacting a vaporous aldehyde with a solid acidic catalyst, e.g. phosphoric acid on a support, at a temperature above 100° C.

Hargis et al., U.S. Pat. No. 3,453,331, teach the production of symmetrical and unsymmetrical ketones from aldehydes by contacting an aldehyde with an oxidized form of a rare earth metal having an atomic number of 59 to 71 supported on an activated alumina. The process is a vapor-phase process.

Other processes are known. See for example the references cited at column 1, lines 23–27, of Canter et al.

SUMMARY OF THE INVENTION

According to this invention, 2-phenyl propanal is converted to 2-indanone by a process comprising contacting at conversion conditions the propanal with a catalyst of the formula

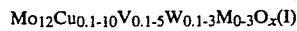

where

M is at least one of tin, lead, chromium, gold, silver, selenium, antimony, bismuth, phosphorus, arsenic, cerium, tellurium, thorium, uranium and a Group IA, IIA, IIB, IVB or VIII element, and x is the number of oxygen atoms determined by the valence requirements of the other elements present.

The process is typically conducted in the vapor phase.

DETAILED DESCRIPTION OF THE INVENTION 2-phenyl propanal, $CH_3CH(\phi)CHO$, (also known as 2-phenylpropionaldehyde and hydratropic aldehyde) is a well known material and is commercially available.

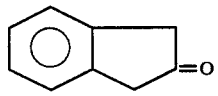

(also known as 2-hydrindone and 2-oxohydrindene) is also a well-known material and is a useful pharmaceutical intermediate, crosslinking agent, and as a monomer in the manufacture of various copolymers.

The catalysts here used are compounds of formula I where M and x are as previously defined. The elements of Groups IA, IIA, IIB, IVB and VIII are defined in the Periodic Table of the Elements as published by Sargent-Welch Scientific Company, copyrighted 1979. Preferably, the subscript of Cu is a number of about 1 to 3, of V a number of about 2 to 4, of W a number of about 0.5 to 2, and M a number greater than 0 (which means at least one promoter is present). Sn, Sb, Te and the Group VIII elements are the preferred promoters with Sn being the most preferred. The promoter elements, as well as W, can be present in either an oxidized or unoxidized (zero valence) state.

The catalysts can be used in either their 100% active form or diluted with other materials, e.g. coated onto a carrier. If diluted, generally any carrier can be used with silica, alumina, silica-alumina, titania, zeolite, zirconia, silicon carbide, carbon, magnesia, compatible organic and inorganic polymers, etc. all being exemplary. Carriers of alumina, silica and silica-alumina are preferred. If a support is used, the catalytic composition is generally present in an amount of at least about 10 weight percent, based on the combined weight of the support and catalytic composition, and preferably in an amount of at least about 30 weight percent.

The catalytic compositions of this invention can be prepared by any one of a number of different methods, the particular method employed being a matter of convenience. These methods include both aqueous and nonaqueous, e.g. alcoholic, methods of preparation. In a typical aqueous preparation, the catalysts are prepared by mixing the appropriate catalyst ingredients in the proper proportions in an aqueous mixture, drying the resulting aqueous slurry with or without a reducing agent, and calcining the product. The ingredients can be added in any order during the preparation procedure but preferably the metallic ingredients are mixed prior to the addition of any nonmetallic ingredients. Ingredients employed can be the oxides, halides, nitrates, acetates or other salts of the particular metals or elements added and particularly preferred is the use of water soluble salts of the metal components. If a support is used, the material comprising the support may be incorporated into the catalyst along with the other ingredients or the catalytic composition can be coated and/or impregnated onto or into the support. After the catalyst ingredients have been combined to form an aqueous slurry, the slurry is taken to dryness and the dried solid obtained is heated in the presence of air, nitrogen, nitric oxide, etc. at a temperature between about 300° C. and 420° C. This calcination can take place outside the catalytic reactor or an in situ activation can be utilized. Other methods of preparation are broadly taught in the art.

As taught by formula I, M can be a combination of two or more promoter elements. Where M is such a combination, the subscript value represents the sum of the elements (e.g. where M is a combination of tin and antimony, the sum of the tin and antimony present is a number of greater than zero to about 3). The individual subscript values of the components, e.g. the individual subscript values for tin and antimony, can vary to convenience.

The exact structure or elemental arrangement of these catalysts is not known but the components are generally present in the form of their oxides or oxide complexes. However, the compositions of formula I are known not to be a mere physical mixture of their components but rather unique entities where the individual components are chemically and/or physically bonded to one another.

Conversion conditions are used in the practice of this invention and these will vary with the catalysts, reactor, etc. employed. This process is a heterogeneous catalytic process, i.e. the catalyst is in the solid state while the propanal is either in the gaseous or liquid state. Preferably, the propanal is in the gaseous state when contacted with the catalyst.

Any temperature at which 2-phenyl propanal is either a liquid or gas can be employed with a typical minimum temperature being about 200° C. and preferably about 250° C. Economy, convenience and degradation of the reactant product and catalyst are the principal constraints upon the maximum temperature employed and a typical maximum temperature is about 550° C. and is preferably about 450° C. Pressure is important primarily as it relates to temperature and pressures ranging from subatmospheric to superatmospheric can be used.

If the propanal is in the gaseous state at the reaction temperature, then it can be used by either itself or diluted with a relatively inert sweep gas, such as nitrogen, argon, helium, carbon dioxide, steam and the like. Likewise, if the propanal is a liquid at the reaction temperature, then it also can be used either alone or with a suitable diluent. Representative diluents include mixed hexanes and heptanes, cyclohexane, benzene, etc.

Contact or residence time can also vary widely, depending upon such variables as the catalyst, reactor, temperature and pressure. Typical contact times range from a fraction of a second to more than several hours with preferred contact times, at least for gaseous phase reactions, between about 0.5 and 10 seconds.

Typically the catalyst is employed in a fixed- or ebullient-bed reactor where the reactant, typically in the gaseous form, is passed over or through the catalyst. Other reactors can be used.

The following examples are illustrative embodiments of this invention. Per pass conversion (PPC) is calculated by dividing the moles of total product times 100 by the moles of reactant fed. The selectivity was calculated by dividing the PPC to the ketone by the PPC of the total product.

SPECIFIC EMBODIMENTS

Catalyst Preparation:
A catalyst consisting, in weight percent, of $$20\% \; (Mo_{12}Cu_2Sn_{0.5}V_3W_{1.2}O_x) \; \text{and} \; 80\% \; Al_2O_3 \quad (II)$$

was prepared by mixing 72 g of molybdenum oxide, 11.4 g of vanadium oxide, 9.2 g of tungsten metal powder, and 3.1 g of stannic oxide in 750 cc of distilled water to yield a gray slurry. The slurry was refluxed with stirring for 2 hours during which time some of the solids dissolved and the color of the mixture turned to a dark blue-black.

Separately, 16.6 g of copper acetate were dissolved in 150 cc of H$_2$O and then admixed with the dark blue-black slurry. The slurry was then refluxed for an additional ½ hour, cooled, evaporated to a thick paste and dried overnight at 110° C. to a dry powder.

Catalyst powder that passed through a 50 U.S. mesh screen was coated onto Al$_2$O$_3$ spheres so that the coating comprised about 20 wt % of the finished particle. The particle was then activated by air calcination for 2 hours.

PROCEDURE

The catalyst was charged to a 20 cc down-flow, fixed-bed reactor. The propanal was then fed to the reactor, together with air and nitrogen at a molar ratio of 1:23:43, at a given temperature and the product collected and analyzed. The off-gas was passed through a cold acetone scrubber where the liquid products were retained. These liquid products were then quantitatively analyzed using Hewlett-Packard gas chromatograph.

EXAMPLE 1

Using the catalyst and procedure described above, 2-phenyl propanal was converted to 2-indanone at 250° C. and atmospheric pressure with a 3 second contact time. The per pass conversion of the propanal was about 28% with a selectivity to the 2-indanone of about 58%.

EXAMPLE 2

Again using the catalyst and procedure described above, the propanal was converted to 2-indanone at 300° C. and atmospheric pressure with a contact time of about 3 seconds. About a 38% per pass conversion of the propanal was obtained with about 38% selectivity to the indanone.

Although the invention has been described in detail by the preceeding examples, this detail is for the purpose of illustration only and is not intended as a limitation upon the spirit and scope of the appended claims.

What is claimed is:

1. A process of converting 2-phenyl propanal to 2-indanone, the process comprising contacting at conversion conditions 2-phenyl propanal with a catalyst of the formula $$Mo_{12}Cu_{0.1-10}V_{0.1-5}W_{0.1-3}M_{0-3}O_x \quad (I)$$

where
M is at least one of tin, lead, chromium, gold, silver, selenium, antimony, bismuth, phosphorus, arsenic, cerium, tellurium, thorium, uranium and a Group IA, IIA, IIB, IVB or VIII element, and
x is the number of oxygen atoms determined by the valence requirements of the other elements present.

2. The process of claim 1 where the subscript value of M is a number greater than 0.

3. The process of claim 2 where M is at least one of Sn, Sb, Te and a Group VIII element.

4. The process of claim 3 where M is Sn.

5. The process of claim 4 where the contacting is conducted at atmospheric pressure and at a temperature between about 200° C. and about 550° C.

* * * * *